(12) United States Patent
Rinker et al.

(10) Patent No.: US 8,212,081 B2
(45) Date of Patent: Jul. 3, 2012

(54) PROCESS FOR PREPARING SUBSTITUTED 1,4-QUINONE METHIDES

(75) Inventors: Stefanie Rinker, Huenxe (DE); Phillip R. James, Tenby (GB); Manfred Neumann, Marl (DE); Oliver Erpeldinger, Wuelfrath (DE); Frank Kraushaar, Essen (DE)

(73) Assignee: Evonik Degussa GmbH, Essen (DE)

( * ) Notice: Subject to any disclaimer, the term of this patent is extended or adjusted under 35 U.S.C. 154(b) by 149 days.

(21) Appl. No.: 12/763,572

(22) Filed: Apr. 20, 2010

(65) Prior Publication Data

US 2010/0267992 A1    Oct. 21, 2010

(30) Foreign Application Priority Data

Apr. 21, 2009    (DE) .................. 10 2009 002 514

(51) Int. Cl.
*C07C 45/27* (2006.01)
*C07C 45/29* (2006.01)

(52) U.S. Cl. ...................... 568/315; 568/436

(58) Field of Classification Search .................. 568/315, 568/436
See application file for complete search history.

(56) References Cited

U.S. PATENT DOCUMENTS

| 5,463,052 | A | 10/1995 | Haga et al. |
| 2007/0208204 | A1 | 9/2007 | Meyer et al. |
| 2009/0114878 | A1 | 5/2009 | Weyler et al. |
| 2010/0168005 | A1 | 7/2010 | Bolli et al. |

FOREIGN PATENT DOCUMENTS

| EP | 0 626 377 A1 | 11/1994 |
| WO | WO 2006/010544 A2 | 2/2006 |
| WO | WO 2006/100633 A1 | 9/2006 |
| WO | WO 2008/029370 A1 | 3/2008 |

OTHER PUBLICATIONS

Brindaban C. Ranu, et al. "A Simple, Efficient and General Procedure for Acetalization of Carbonyl Compounds and Deprotection of Acetals under the Catalysis of Indium (III) Chloride" Adv. Synth. Catal. 2004, vol. 346, (pp. 446-450).

weizhong Gong, et al. "Sulfamic Acid as a Cost-Effective and Recyclable Catalyst for Protection of Carbonyls to Acetals and Ketals Under Mild Conditions" Synthetic Communications 2004, vol. 34, (pp. 4243-4247).

Ran Ruicheng, et al. "Polymer-Supported Lewis Acid Catalysts. I. Polystyrene-Gallium Trichloride Complex." J. Macromol. Sci.-Chem. 1987, vol. A24(6), (pp. 669-679).

B. Roth, et al. "2,4-Diamino 5-benzylpyrimidines and Analogues as Antibacterial Agents. 9. Lipophilic Trimethoprim Analogues as Antigonococcal Agents" J. Med. Chem. 1988, vol. 31, (pp. 122-129).

Paul C. Unangst, et al. "Synthesis and Biological Evaluation of 5-[[3,5-Bis(1,1-dimethylethyl)-4-hydroxyphenyl]methylene]oxazoles, -thiazoles, and -imidazoles: Novel Dual 5-Lipoxygenase and Cyclooxygenase Inhibitors with Antiinflammatory Activity" J. Med. Chem. 1994 vol. 37, (pp. 322-328).

Charles M. Orlando, "Quinone Methide Chemistry. Benzylic Oxidative Methoxylation of 2,6-di-tert-butyl-p-cresol" J. Org Chem. 1970, vol. 35, (pp. 3714-3717).

Masanao Inagaki, et al. "Highly E-Selective and Effective Synthesis of Antiarthritic Drug Candidate S-2474 Using Quinone Methide Derivatives" J. Org. Chem. 2002, vol. 67, (pp. 125-128).

Rangam Gopinath, et al."Tetrabutylammonium Tribromide (TBATB) as An Efficient Generator of HBr for an Efficient Chemoselective Reagent for Acetalization of Carbonyl Compoounds" J. Org. Chem. 2002, vol. 67, (pp. 5842-5845).

Nao Hamada, et al. "An Efficient and Versatile Procedure for the Synthesis of Acetals from Aldehydes and Ketones Catalyzed by Lithium Tetrafluoroborate" Synlett. 2004, vol. 6, (pp. 1074-1076).

Yuying Du, et al. "Bronsted Acidic Ionic Liquids as Efficient and Recyclable Catalysts for Protection of Carbonyls to Acetals and Ketals Under Mild Conditions" Synthetic Communicatons. 2005, vol. 35, (pp. 2703-2708).

Seung Hwan Lee, et al. "An efficient Protection of Carbonyls and Deprotection of Acetals using Decaborane" Tetrahedron Letters. 2002, vol. 43, (pp. 2699-2703).

*Primary Examiner* — Sikarl Witherspoon

(74) *Attorney, Agent, or Firm* — Oblon, Spivak, McClelland, Maier & Neustadt, L.L.P.

(57) ABSTRACT

A method for preparing a substituted 1,4-quinone methide from a 3,5-disubstituted 4-hydroxybenzaldehyde is provided. Also provided is a method to prepare a 3,5-disubstituted 4-hydroxybenzaldehyde from the corresponding 2,6-disubstituted phenol.

19 Claims, No Drawings

PROCESS FOR PREPARING SUBSTITUTED 1,4-QUINONE METHIDES

BACKGROUND OF THE INVENTION

1. Field of the Invention

The present invention relates to a process for preparing substituted 1,4-quinone methides of the formula (I) from 3,5-disubstituted 4-hydroxybenzaldehydes, and also to a process for preparing the 3,5-disubstituted 4-hydroxybenzaldehydes from the corresponding 2,6-disubstituted phenols.

2. Description of the Related Art

7-Methoxy- and 7-ethoxy-substituted 1,4-quinone methides are known in the literature as important isolable intermediates for the synthesis of active pharmaceutical ingredients. In addition, some 1,4-quinone methides can be used to prevent undesired polymerization of olefinically unsaturated monomers.

The preparation of 2,6-di-tert-butyl-4-methoxy-methylenecyclohexane-2,5-dienone and of 2,6-di-tert-butyl-4-ethoxymethylenecyclohexane-2,5-dienone is described by Inagaki et al. both in J. Org. Chem. 2002, 67, 125-128 and in EP 0 626 377 A1. This involves reacting a mixture of 3,5-di-tert-butyl-4-hydroxy-benzaldehyde with an excess of trimethyl orthoformate, absolute methanol and xylene in the presence of ammonium chloride as a catalyst to give the corresponding acetal, by heating the reaction mixture under reflux for a few hours. Subsequently, a distillation is performed, xylene is added as an additional solvent, the mixture is cooled, and then the catalyst—the ammonium chloride—is filtered off. In order to achieve the elimination of the alcohol from the acetal to give the substituted 1,4-quinone methide, in both publications, the filtrate is heated and thus methanol and xylene are distilled off. This concentrates the product, which is filtered and then recrystallized in hexane or in a mixture of petroleum ether and ligroin.

The preparation of the corresponding acetal of the 3,5-disubstituted 4-hydroxybenzaldehyde by reaction with orthoformate and/or alcohols is described in numerous publications:

Orlando describes, in J. Org. Chem. 1970, 35, 3714-3717, an almost identical process for preparing the acetal to that of Inagaki et al. in their two publications. Here too, 3,5-di-tert-butyl-4-hydroxybenzaldehyde is heated under reflux with an excess of trimethyl orthoformate and absolute methanol in the presence of ammonium chloride as a catalyst, although no additional solvent is used in this process. After the filtration, the acetal is isolated by concentration and recrystallization from hexane.

Roth et al. described, in J. Med. Chem. 1988, 31, 122-129, a process for preparing the acetal from 3,5-disubstituted 4-hydroxybenzaldehydes, which also involves heating a mixture of 3,5-diisopropyl-4-hydroxybenzaldehyde, trimethyl orthoformate, ammonium chloride and methanol under reflux for a few hours. Subsequently, the reaction mixture is allowed to cool, an aqueous ammonium hydroxide solution is added, the mixture is extracted with dichloromethane and washed, and the organic phase is dried and concentrated to dryness. The desired acetal can then be crystallized from hot hexane.

The preparation of acetals of other 4-hydroxybenzaldehydes with trimethyl orthoformate and/or methanol in the presence of various catalysts is described in numerous publications. For instance, Du et al. describe, in *Synthetic Communications* 2005, 35, 2703-2708, the use of ionic liquids as a catalyst. The use of amidosulphonic acid as a catalyst is described by Gong et al. in Synthetic Communications 2004, 34, 4243-4247. Lithium tetrafluoroborate as a suitable catalyst is described by Hamada et al. in Synlett 2004, 6, 1074-1076. While Ranu et al. describe the use of indium chloride as a catalyst in Adv. Synth. Catal. 2004, 346(4), 446-450. Gopinath et al. describe, in J. Org. Chem. 2002, 67, 5842-5845, a process for preparing the acetal in the presence of tetrabutylammonium chloride as a catalyst. The use of the highly toxic decaborane as a catalyst is described by Lee et al. in Tetrahedron Letters 2002, 43, 2699-2703. A copolymer with gallium trichloride as suitable catalyst is described by Ruicheng et al. in J. Macromol. Sci.-Chem. 1987, A24(6), 669-679.

The literature describes many different ways of preparing 3,5-substituted 4-hydroxybenzaldehydes. The main starting materials here are the corresponding 2,6-disubstituted phenols or 2,6-disubstituted 4-methylphenols. One method of preparing these 3,5-substituted 4-hydroxybenzaldehydes is the formylation of the 2,6-disubstituted phenols in the para position with urotropin.

For instance, Bolli et al. described, in the two PCT publications, WO 2006/100633 A1 and WO 2006/010544 A2, the reaction of, respectively, 2-ethyl-6-methylphenol and 2,6-diethylphenol with an excess of urotropin in the presence of acetic acid. After distilling off a first solvent fraction, the reaction mixture is heated under reflux for three hours and diluted with water, and then the corresponding 4-hydroxybenzaldehyde is extracted with ethyl acetate. The yields reported are 31% and 40% respectively.

Unangst et al. described, in J. Med. Chem. 1994, 37, 322-328, the reaction of 3,5-diphenylphenol with an excess of urotropin in the presence of acetic acid. This reaction involves adding water, heating the reaction mixture under reflux and removing distillate until a temperature of 114° C. is achieved. The reported yield is 64%.

A process with a yield of 81% is described by Roth et al. in J. Med. Chem. 1988, 31, 122-129. Here, 3,5-diisopropylphenol is reacted with an excess of urotropin in the presence of glacial acetic acid and water. According to the described method, a distillate is removed before the reaction mixture is heated under reflux.

DETAILED DESCRIPTION OF THE INVENTION

It is an object of the present invention to provide a process for preparing substituted 1,4-quinone methides of the formula (I), which may be suitable for industrial scale application and may thus be economically viable and not intensive in terms of plant resources. In addition, the process of the present invention is applicable not only to the preparation of the 7-methoxy- and 7-ethoxy-substituted 1,4-quinone methides described in the literature, but also to the preparation of further substituted 1,4-quinone methides of formula (I).

Surprisingly, a broadly applicable process for preparing substituted 1,4-quinone methides of the formula (I) has been found, wherein a (thio)acetal is first formed from 4-hydroxybenzaldehydes of the formula (II), which may then be converted directly to the desired substituted 1,4-quinone methides in a further step by thermally induced elimination of alcohol or thiol. With this process according to the invention, not only may the 7-methoxy and 7-ethoxy-substituted 1,4-quinone methides described in the literature be prepared, but completely new compounds may also be obtained.

In the process according to the present invention, the (thio)acetals may be formed, in contrast to conventional methods, using inexpensive, nontoxic and halogen-free catalysts, for example, organic sulphonic acids, sulphuric acid and/or hydrogensulphates thereof. Halogen-free preparation may thus be possible. Specifically in industrial scale processes, this may be an important advantage owing to the risk of stress-cracking corrosion in the case of use of halides in the reactor. It is completely surprising that inexpensive nontoxic substances which catalyse acetal formation may also be used, whereas conventionally known methods, apart from halogenated compounds, propose only expensive, toxic and/or CMR-active compounds, such as decaborane, as catalysts.

In addition, according to the method of the present invention, the proportional amount of the catalyst may be lowered compared to conventionally known processes, and even with the lower proportion of catalyst the conversion may surprisingly increase. In addition, in contrast to many conventionally known processes, the proportion of the expensive orthoformate reactant may be lowered significantly, while achieving equal conversions of more than 90%. Since the process according to the invention in the first process stage may not require an additional solvent, it may additionally be possible to significantly improve the space-time yield.

In the process according to the present invention, 3,5-disubstituted 4-hydroxybenzaldehydes of the formula (II) may be used as the starting reactant. Further, according to the present invention, it may also be possible to improve the upstream process step for the preparation of the 3,5-disubstituted 4-hydroxybenzaldehyde from a 2,6-disubstituted phenol. Thus, the inventors have surprisingly discovered, that both through modification of the sequence of metered addition and through the use of a reaction temperature below the reflux temperature, yields of more than 80% may be achieved. In addition, it was surprising that in a particular embodiment of the present invention the molar amount of urotropin based on the 2,6-disubstituted phenol used may be lowered to below a ratio of urotropin to 2,6-disubstituted phenol of 1:1 without yield losses.

This and other objects have been achieved by the present invention, the first embodiment of which includes a process for preparing a substituted 1,4-quinone methide of formula (I)

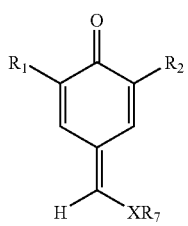

formula (I)

wherein
$R_1$ and $R_2$ are each independently hydrogen, optionally substituted $(C_1-C_{15})$-alkyl, $(C_3-C_{15})$-cycloalkyl or $(C_6-C_{14})$-aryl,
$R_7$ is optionally substituted $(C_1-C_{15})$-alkyl, $(C_3-C_{15})$-cycloalkyl or $(C_6-C_{14})$-aryl, and
X is O or S,
comprising:
reacting a 3,5-disubstituted 4-hydroxybenzaldehyde of formula (II)

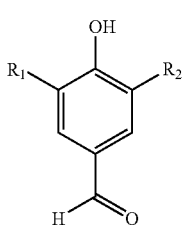

formula (II)

wherein $R_1$ and $R_2$ are each as defined above,
with an orthoformate of formula (III)

formula (III)

wherein $R_4$, $R_5$ and $R_6$ are each independently optionally substituted $(C_1-C_{15})$-alkyl, $(C_3-C_{15})$-cycloalkyl or $(C_6-C_{14})$-aryl,
and an alcohol and/or thioalcohol ((thio)alcohol) of formula (IV)

formula (IV)

wherein
$R_3$ is an optionally substituted $(C_1-C_{15})$-alkyl, $(C_3-C_{15})$-cycloalkyl or $(C_6-C_{14})$-aryl, and
X is O or S,
in the presence of a at least one catalyst selected from the group consisting of a free or solid-phase-bound organic sulphonic acid, sulphuric acid, a hydrogensulphate, an organic or inorganic phosphorus acid, a dihydrogen or hydrogen salt of an organic or inorganic phosphorous acid, fuming nitric acid and boric acid, to obtain an acetal; and eliminating the alcohol or thiol from the obtained acetal to yield the substituted 1,4-quinone methide of formula (I).

In a second embodiment, the present invention provides a process for preparing a 3,5-disubstituted 4-hydroxybenzaldehyde of formula (II)

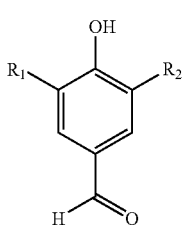

formula (II)

wherein
$R_1$, $R_2$ are each independently, hydrogen, optionally substituted $(C_1-C_{15})$-alkyl, $(C_3-C_{15})$-cycloalkyl or $(C_6-C_{14})$-aryl,
comprising:
reacting a 2,6-disubstituted phenol of formula (VII)

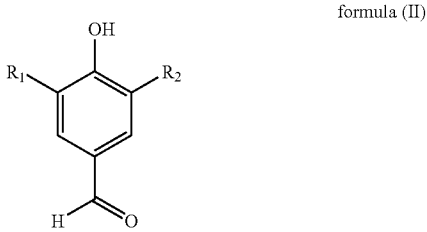

formula (VII)

wherein $R_1$ and $R_2$ are each as defined above,
with urotropin in a solvent mixture consisting of glacial acetic acid and water;

wherein a reaction temperature is maintained at least 2° C. below a reflux temperature of the reaction mixture over the entire reaction time.

In a further embodiment, the present invention provides a process for preparing a substituted 1,4-quinone methide of formula (V)

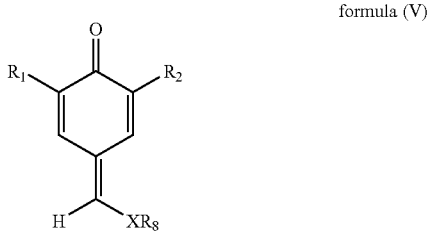

formula (V)

wherein
$R_1$ and $R_2$ are each independently hydrogen, optionally substituted $(C_1$-$C_{15})$-alkyl, $(C_3$-$C_{15})$-cycloalkyl or $(C_6$-$C_{14})$-aryl,
$R_8$ is an optionally substituted $(C_3$-$C_{15})$-alkyl, $(C_3$-$C_{15})$-cycloalkyl or $(C_6$-$C_{14})$-aryl, and
X is O or S,
comprising:
reacting a substituted 1,4-quinone methide of formula (I)

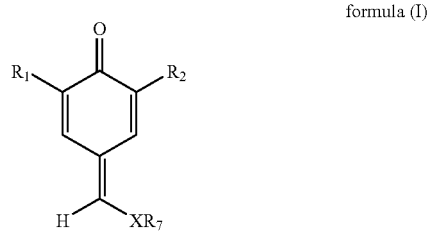

formula (I)

wherein $R_7$ is an unsubstituted $(C_1$-$C_2)$-alkyl group,
X is O, and
$R_1$ and $R_2$ are each as defined above,
with an alcohol or thioalcohol of formula (VI)

formula (VI)

wherein X is O or S, and
$R_8$ is as defined above.

For acetal formation in the process according to the present invention, preference may be given to using, as the starting reactant, a 3,5-disubstituted 4-hydroxybenzaldehyde of formula (II) wherein $R_1$ and $R_2$, independently of one another may be $(C_1$-$C_{15})$-alkyl, $(C_3$-$C_{15})$-cycloalkyl and/or $(C_6$-$C_{14})$-aryl groups; preferably $R_1$ and $R_2$ may be $(C_1$-$C_4)$-alkyl and/or $(C_3$-$C_{15})$-cycloalkyl groups. Particular preference may be given to a 3,5-disubstituted 4-hydroxybenzaldehyde of formula (II) wherein $R_1$ and $R_2$ are independently $(C_1$-$C_4)$-alkyl groups, most preferably branched $(C_3$-$C_4)$-alkyl groups, such as tert-butyl or isopropyl groups.

According to the present invention $R_1$ and $R_2$ may be substituted or unsubstituted. In one preferred embodiment, $R_1$ and $R_2$ may be unsubstituted.

In the context of the present invention, substituents may be selected from —COOR, —OH, —OR, -halogen, —NR$_2$, =O and —CO—NR$_2$, where R=hydrogen, $(C_1$-$C_{15})$-alkyl, $(C_3$-$C_{15})$-cycloalkyl and/or $(C_6$-$C_{14})$-aryl groups, which may in turn be substituted by at least one of these substituents.

Further reactants used for the acetal formation in the process according to the present invention are orthoformates of formula (III), wherein the substituents $R_4$, $R_5$ and $R_6$ may preferably be $(C_1$-$C_{15})$-alkyl or $(C_3$-$C_{15})$-cycloalkyl groups, more preferably $(C_1$-$C_4)$-alkyl groups. According to the present invention, $R_4$, $R_5$ and $R_6$ may preferably be unsubstituted.

In a particularly preferred embodiment of the process according to the invention, orthoformates which have $(C_1$-$C_2)$-alkyl groups as substituents $R_4$, $R_5$ and $R_6$ may be used. Very particular preference may be given to using orthoformates wherein $R_4$, $R_5$ and $R_6$ are all identical. Trimethyl orthoformate may be particularly preferred as the orthoformate of formula (III) in an embodiment of the process according to the present invention.

In addition to the 3,5-disubstituted 4-hydroxy-benzaldehydes of formula (II) and the orthoformates of formula (III), alcohols and/or thioalcohols of the formula (IV), where the substituent $R_3$ is preferably unsubstituted, may also be used for the acetal formation of the process according to the invention. $R_3$ may preferably be a $(C_1$-$C_{15})$-alkyl or $(C_3$-$C_{15})$-cycloalkyl group and more preferably a $(C_1$-$C_4)$-alkyl group.

In a further particularly preferred embodiment of the process according to the present invention, an alcohol of formula (IV) may be used, more preferably an alcohol wherein $R_3$ may be a phenyl or $(C_1$-$C_{15})$-alkyl group and most preferably a $(C_1$-$C_4)$-alkyl group. In particular, the alcohol of formula (IV) may be methanol or ethanol.

In a highly preferred embodiment of the present invention, orthoformates and alcohols and/or thioalcohols, wherein the substituents $R_4$, $R_5$ and $R_6$ of the orthoformate are identical to the substituent $R_3$ of the alcohol and/or thioalcohol are employed.

When the substituents $R_3$ and $R_4$, $R_5$ and $R_6$ are different, mixtures of different substituted 1,4-quinone methides may form. In the case of use of a thioalcohol, the major product may be a quinone methide wherein X is S and $R_7$ is $R_3$ of the thioalcohol. In contrast, in the case of use of orthoformates and (thio)alcohols with different substituents $R_3$ and $R_4$, $R_5$ and $R_6$, preferably the correspondingly substituted 1,4-quinone methide of the formula (I) of the least volatile (thio) alcohol may form.

The catalysts used in the process according to the present invention may preferably be free or solid-phase-bound organic sulphonic acids, sulphuric acid, hydrogensulphates, organic or inorganic phosphorus acids, the dihydrogen and hydrogen salts thereof, fuming nitric acid and/or boric acid. Preferred catalysts are free or solid-phase-bound organic sulphonic acids, sulphuric acid and/or hydrogensulphates, and particularly preferred may be catalysts of alkylbenzenesulphonic acids, polymers which have sulphonic acid groups or hydrogensulphates of the alkali metals and alkaline earth metals. The most preferred catalysts may be hydrogensulphates of the alkali metals and alkaline earth metals, especially potassium hydrogensulphate or sodium hydrogensulphate.

The organic sulphonic acids used may be alkylbenzenesulphonic acids, for example p-toluene sulphonic acid or dodecylbenzenesulphonic acid, or polymers which have sulphonic acid groups.

The use of solids as catalysts may have the advantage that this catalyst can be removed from the reaction mixture in a simple manner, for example by filtration. Compared to conventional processes catalyzed with ammonium chloride the process according to the invention may enable production on an industrial scale to provide a product without halides. Thus, there may be no need for any complicated corrosion protection of the plant parts according to the process of the present invention. Preferably, the catalysts used in the process according to the present invention may be inexpensive, halogen-free and non-toxic acids.

The molar ratio of the 3,5-disubstituted 4-hydroxybenzaldehyde of the formula (II) to the catalyst in the process according to the invention is preferably from 1:0.0002 to 1:0.5, preferentially from 1:0.0005 to 1:0.2, more preferably from 1:0.001 to 1:0.1 and most preferably from 1:0.005 to 1:0.05.

According to the process of the present invention the molar ratio of the 3,5-disubstituted 4-hydroxybenzaldehyde of formula (II) to the orthoformate may be from 1:0.5 to 1:10, the ratio preferably being 1:0.9 to 1:5 and more preferably from 1:1 to 1:2. The lowering of the amount of the relatively expensive orthoformate allows the operating costs of an industrial scale plant to be lowered, without the conversions being reduced as a result.

The (thio)acetal formation in the process according to the invention may be performed either with an additional solvent (A) or without an additional solvent. Suitable additional solvents (A) include solvents which are inert toward the 4-hydroxybenzaldehyde, alcohol, thiol and orthoformate reactants used and to the (thio)acetal. Preferred solvents (A) may be aromatic solvents such as toluene, ethylbenzene and/or xylenes.

In a particularly preferred embodiment of the process according to the invention, the 4-hydroxybenzaldehyde may be converted to the (thio)acetal in the absence of an additional solvent (A). In this way, the space-time yield of the process according to the invention may be improved.

The 4-hydroxybenzaldeyde may be converted to the (thio)acetal in the process according to the invention by heating under reflux, preferably for 0.5 to 10 hours and more preferably for 1 to 5 hours.

The conversion of the 3,5-disubstituted 4-hydroxybenzaldehyde to the corresponding (thio)acetal may be performed at different pressures including 0.1 to 10 bar, preferably 0.5 to 5 bar and most preferably 0.8 to 1.2 bar. In a particularly preferred embodiment of the present invention, this process stage is effected at atmospheric pressure. However, in the case of use of some thioalcohols, having low boiling points, working under pressure may be advisable.

The (thio)acetal obtained according to the process of the present invention may be isolated by conventional isolation methods, including concentration of the solution, extraction, filtration, crystallization, and other methods know to one of skill in the art. The (thio)acetal may preferably not be isolated before the elimination of the alcohol, but converted directly from the solution to the desired product—the substituted 1,4-quinone methide of the formula (I).

In the process according to the present invention, before the elimination of the (thio)alcohol from the (thio)acetal, the excess orthoformate and the excess alcohol or thioalcohol may be removed—preferably by distillation. If the (thio) acetal is not to be isolated, it may be advisable to add an additional solvent (B) before distillative removal of the orthoformate and of the alcohol or thioalcohol. This may achieve the effect that the (thio)acetal remains in solution even after the distillative removal of the orthoformate and of the alcohol or thioalcohol.

Suitable additional solvents (B) may be solvents which have a higher boiling point than the alcohol and/or thioalcohol used and are inert toward the (thio)acetal and the substituted 1,4-quinone methide to be formed. The boiling point of the solvent (B) may be at least 100° C., preferably from 110° C. to 250° C. In addition, a solvent (B) which may be capable of keeping the acetal formed in solution is preferred. In a particular embodiment of the present invention, the solvent (B) may be aromatic solvents including toluene, ethylbenzene, o-, m- or p-xylene, and mixtures of these and other aromatic solvents. It may also be possible to use mixtures of aromatic hydrocarbons with a correspondingly defined boiling point range as the additional solvent (B).

The distillation of the excess orthoformate and of the excess alcohol or thioalcohol is preferably carried out until the reaction mixture has attained the boiling point of the additional solvent (B). This removal can be effected either under atmospheric pressure or under reduced pressure.

In the process according to the present invention, the catalyst may likewise be removed from the (thio)acetal before the thermal elimination of the (thio)alcohol, for example by mechanical separation processes. Mechanical separation may be particularly suitable for removal of solid catalysts. Suitable mechanical separation processes according to the present invention include filtration, sedimentation or centrifugation with subsequent decantation. Especially in the case of catalysts present in solid form, it may be preferred to remove the catalyst before the thermal elimination of the (thio)alcohol from the (thio)acetal, in order that the column may not be contaminated by introduced solids.

Liquid catalysts, or traces of solid catalysts, may preferably be neutralized with a base. Particularly preferred bases are non-nucleophilic or sterically hindered amines and inorganic salts, for example, carbonates. Removal of the neutralization product may not be necessary.

The sequence of removal or neutralization of the catalyst, of addition of a solvent (B) and of the removal of the excess (thio)alcohol and of the excess orthoformate may be varied arbitrarily as required depending on the catalyst, (thio)alcohol and orthoformate, without yield losses.

To eliminate the (thio)alcohol from the (thio)acetal, the acetal-containing reaction mixture of the process according to the present invention is preferably heated to the boiling temperature of the solvent (B), preferably to at least 100° C., more preferably to 110 to 250° C., and the (thio)alcohol released may be removed from the reaction mixture, preferably immediately after formation thereof, by chemical and/or physical methods. The (thio)alcohol eliminated by thermal induction may be removed from the reaction mixture by conventional methods known to one of skill in the art. For instance, the alcohol released may be chemically bound by adding suitable reagents, for example, anhydrides. However, physical methods, for example the use of a molecular sieve in the case of short-chain (thio)alcohols, may also be employed.

In an embodiment of the present invention, the (thio)alcohol released may preferably be removed by distillation. According to this distillation method the acetal-containing reaction mixture may be heated to at least 100° C., preferably to 110 to 250° C., in the course of which an additional solvent (C) may be continuously metered in, while the alcohol and/or thioalcohol released may be simultaneously removed from the reaction mixture together with the additional solvent (C).

In a preferred embodiment of the present invention additional solvent (C) equal in amount to the amount of distillate, substantially consisting of (thio)alcohol and solvent (A, B and C), which is distilled off, may be metered into the reaction mixture. The additional solvent (C) may serve to more easily remove the excess alcohol and/or thioalcohol from the reaction mixture, and hence to achieve the elimination of the (thio)alcohol from the (thio)acetal. The elimination of the alcohol may be at lower temperatures with simultaneous pressure reduction. In addition to the shift in equilibrium in favour of the substituted 1,4-quinone methide of the formula (I), this process step may also provide the advantage that traces of water are likewise removed from the reaction mixture, and hence the back-reaction of the substituted 1,4-quinone methide to the 4-hydroxybenzaldehyde may be substantially suppressed.

Suitable additional solvents (C) may be solvents which have a boiling point of at least 100° C., preferably of 110 to 250° C., and are inert toward the (thio)acetal and the substituted 1,4-quinone methide of the formula (I). Particularly preferred solvents may be aromatic solvents including toluene, ethylbenzene, o-, m- or p-xylene, and mixtures of these aromatic solvents. Mixtures of aromatic hydrocarbons with a corresponding defined boiling point range may also be the additional solvent (C). In a very particularly preferred embodiment of the process according to the invention, the solvents (A), (B) and (C) may be identical.

In a further embodiment of the process according to the present invention, two different solvents may be used, in which case the solvent (C) preferably has a higher boiling point than the solvent (B). This may be advantageous when the substituted 1,4-quinone methide is to be present in a solvent which is not very suitable for the distillation of the excess orthoformate and of the excess alcohol or thioalcohol.

In a further preferred embodiment of the present invention, a process for preparing a substituted 1,4-quinone methide of formula (V)

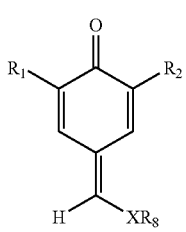

formula (V)

wherein
R$_1$ and R$_2$ are each independently hydrogen, optionally substituted (C$_1$-C$_{15}$)-alkyl, (C$_3$-C$_{15}$)-cycloalkyl or (C$_6$-C$_{14}$)-aryl,
R$_8$ is an optionally substituted (C$_3$-C$_{15}$)-alkyl, (C$_3$-C$_{15}$)-cycloalkyl or (C$_6$-C$_{14}$)-aryl, and
X is O or S,
is provided. The process comprises:
reacting a substituted 1,4-quinone methide of formula (I)

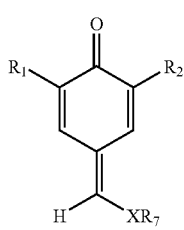

formula (I)

wherein
R$_7$ is an unsubstituted (C$_1$-C$_2$)-alkyl group,
X is O, and
R$_1$ and R$_2$ are each as defined above,
with an alcohol or thioalcohol of formula (VI)

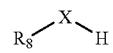

formula (VI)

wherein X is O or S, and R$_8$ is as defined above and the substituted 1,4-quinone methide of formula (I) is preferably formed by the process according to the present invention.

In this case, the reaction mixture consisting of the substituted 1,4-quinone methide of the formula (I) where R$_7$=unsubstituted (C$_1$-C$_2$)-alkyl group and X=O, where R$_1$ and R$_2$ are each as defined in formula (V), and the (thio)alcohol of the formula (VI) of the process according to the invention may preferably be heated to boiling temperature of the corresponding solvent, preferably to at least 100° C., more preferably to 110 to 250° C., and the methanol and/or ethanol may be removed directly from the reaction mixture by chemical and/or physical methods. The methanol and/or ethanol eliminated by thermal induction may be removed from the reaction mixture by conventional methods. For instance, the methanol and/or ethanol released may be chemically bound by adding suitable reagents, for example anhydrides. However, physical methods, for example the use of a molecular sieve, may also be employed.

In the process according to the invention, this removal of the methanol and/or ethanol released is preferably effected by distillation. This method involves heating the reaction mixture to at least 100° C., preferably to 110 to 250° C., in the course of which an additional solvent (D) may be metered in continuously, while the methanol and/or ethanol released is simultaneously removed from the reaction mixture together with the additional solvent (D). Particular preference is given here to metering in as much additional solvent (D) into the reaction mixture as the amount of methanol and/or ethanol and solvents which is distilled off.

Suitable additional solvents (D) are solvents which have a boiling point of at least 100° C., preferably of 110° C. to 250° C., and are inert toward reaction participants and also the desired product. In a particular embodiment of the present invention, aromatic solvents including toluene, ethylbenzene, o-, m- or p-xylene, and mixtures thereof are preferred. It may also be possible to use mixtures of aromatic hydrocarbons with a corresponding defined boiling point range as the additional solvent (D). In a very particularly preferred embodiment of the process according to the invention, the solvents (A), (B), (C) and (D) are identical.

In this way, substituted 1,4-quinone methides of the formula (V) with a substituent R$_8$ which has more than two carbon atoms may be readily obtained. This variant of the process according to the invention provides the advantage that a multitude of derivatives may be prepared from a single intermediate, the substituted 1,4-quinone methide of the formula (I) where $R_7$ is unsubstituted $(C_1-C_2)$-alkyl group and X is O, the individual preparation processes differing only in the last process step. This may be of particular interest especially in active pharmaceutical ingredient research.

The quinone methide solution obtained by the process according to the present invention may be used further directly. In the case that the quinone methide solution cannot be used directly, the substituted 1,4-quinone methide may be isolated by cooling the product mixture, crystallizing and removing the product, which may optionally be purified, for example by recrystallization. It may also be helpful to completely remove the solvent for the crystallization process, and exchange it for a solvent in which the substituted 1,4-quinone methide has a lower solubility. In this way, the crystallization process may be simplified or accelerated. The substituted 1,4-quinone methide may also be obtained by a complete or partial removal of the solvent.

The 3,5-disubstituted 4-hydroxybenzaldehyde of formula (II) used in the process according to the invention may be prepared either proceeding from 2,6-disubstituted phenol or proceeding from 2,6-disubstituted 4-methylphenol by conventionally known processes. A particularly suitable process has been found to be one wherein a 2,6-disubstituted phenol of the formula (VII) is reacted with urotropin in a solvent mixture consisting of glacial acetic acid and water at temperatures which are at least 2° C. below the reflux temperature of the reaction mixture over the entire reaction time.

The reactants used for the process according to the present invention for preparing the 3,5-disubstituted 4-hydroxybenzaldehyde may preferably be a 2,6-disubstituted phenol or mixtures of such compounds, where the substituents in the 2 and 6 positions correspond to the substituents $R_1$ and $R_2$ in formula (II).

Preference may be given to using 2,6-disubstituted phenols which have $(C_1-C_{15})$-alkyl, $(C_3-C_{15})$-cycloalkyl and/or $(C_6-C_{14})$-aryl groups, more preferably $(C_1-C_4)$-alkyl and/or $(C_3-C_{15})$-cycloalkyl groups as substituents $R_1$ and $R_2$. Very particular preference is given to using 2,6-disubstituted phenols with $(C_1-C_4)$-alkyl groups as substituents $R_1$ and $R_2$. In a particularly preferred embodiment of the process according to the present invention, 2,6-disubstituted phenols which have branched $(C_3-C_4)$-alkyl groups, such as tert-butyl or isopropyl groups, may be used.

In particular, the 2,6-disubstituted phenols used have unsubstituted groups as substituents $R_1$ and $R_2$.

The process according to the present invention may be advantageous in its freedom from halogen, since preference is given to not using any halogenated compounds.

The molar ratio of the 2,6-disubstituted phenol to urotropin may preferably be less than or equal to 1:1 and in a particularly preferred embodiment the molar ratio may be from 1:1 to 1:0.8.

The ratio of glacial acetic acid to water is preferably selected such that a reaction temperature of 115° C.±10° C. may be established without any need to distil off water.

As a result, the process according to the present invention may have improved efficiency, because the process step of water removal common to conventionally known processes may be eliminated. The molar ratio of acetic acid to water may preferably be from 1:1 to 20:1, more preferably from 1.1:1 to 10:1 and most preferably from 1.2:1 to 5:1.

The 2,6-disubstituted phenol, the glacial acetic acid, the water and the urotropin may be combined in any desired sequence. Preference may be given to dissolving the 2,6-disubstituted phenol in glacial acetic acid, and adding urotropin and finally the water. The mixing of the components may also be effected either at room temperature or at elevated temperatures.

According to the process of the present invention the reaction temperature throughout the conversion of the 2,6-disubstituted phenol to the 3,5-disubstituted 4-hydroxybenzaldehyde may be a temperature a few degrees below the reflux temperature, preferably at least 2° C., more preferably at least 3° C. and most preferably 5° C. below the reflux temperature. This may be advantageous because while the reaction temperature may be sufficient for a virtually complete conversion of the 2,6-disubstituted phenol to the 3,5-disubstituted 4-hydroxybenzaldehyde, the temperature is insufficient to reflux the reaction mixture and thus to soil or even to block the column with the product, which may be solid, which collects at the liquid surface. Especially in industrial scale processes, this is an undesired effect. Moreover, it has been found that a process which works with a reaction temperature below the reflux temperature also allows the purity of the substituted 1,4-quinone methide to be improved. In a particular preferred embodiment of this process according to the present invention, the reaction mixture may be heated to a temperature of 115° C.±10° C. over the entire reaction time. The reaction temperature over the entire reaction time is preferably not less than 10° C. below the reflux temperature.

In the context of this invention, the entire reaction time is understood to mean the time span in which the desired reaction temperature for the reaction of the 2,6-disubstituted phenol with the urotropin is attained and maintained. In the context of this invention, the heating and cooling phases are not included in the entire reaction time, even though reactions of the 2,6-disubstituted phenol can already or still be observed in these phases.

The reaction mixture in the reaction of the 2,6-disubstituted phenol and urotropin may preferably be heated to the desired reaction temperature and maintained at the reaction temperature for 1 to 10 hours, preferably for 2 to 7 hours and more preferably for 3 to 6 hours.

Due to the different substituents in the $R_1$ and $R_2$ positions, the solubility and the melting point of the 3,5-disubstituted 4-hydroxybenzaldehydes may be very different. Depending on the substitution pattern of the 4-hydroxybenzaldehyde, different methods may be used to isolate the 3,5-disubstituted 4-hydroxybenzaldehyde. Isolation methods may include the following:

(A) Filtering off the precipitated solid, in which case the filtrate obtained after the filtration may be sent to a further conversion of 2,6-disubstituted phenols to the 3,5-disubstituted 4-hydroxy-enzaldehyde.

(B) Adding water, to precipitate the 3,5-disubstituted 4-hydroxybenzaldehyde, with further workup according to (A).

(C) Extracting with a suitable solvent, then washing the extract with water and distillatively removing the solvent. The solvents used here may be solvents which are water-immiscible or do not have good water miscibility, preference being given to using aromatic solvents such as toluene, ethylbenzene, xylenes, or mixtures thereof.

(D) Distilling off acetic acid and water, in which case the residue consisting predominantly of the 3,5-disubstituted 4-hydroxybenzaldehyde may subsequently be washed with water, to remove the salts which form in the reaction.

Having generally described this invention, a further understanding can be obtained by reference to certain specific examples which are provided herein for purposes of illustration only, and are not intended to be limiting unless otherwise specified.

EXAMPLES

Examples 1-4

7 g (30 mmol) of 3,5-di-tert-butyl-4-hydroxybenzaldehyde were initially charged in a reaction flask and admixed with a mixture consisting of 14.5 ml of methanol and 14.2 g of trimethyl orthoformate. Subsequently, 5 mmol of the catalyst according to Table 1 were added. The reaction mixture was heated to reflux while stirring. After three hours, the reaction mixture was cooled to room temperature and the conversion of the aldehyde was determined by gas chromatography. The conversions of the aldehydes as a function of the catalyst used are shown in Table 1.

TABLE 1

| Example | Catalyst | Conversion of the aldehyde (in GC %) |
|---|---|---|
| CE 1 | Ammonium chloride | 98.6 |
| 1 | p-toluenesulphonic acid | 95.0 |
| 2 | Sulphuric acid | 91.1 |
| 3 | Potassium hydrogensulphate | 99.4 |
| 4 | Sulphonated polystyrene (Lewatit ® K2649) | 98.6 |

CE: Comparative example

Examples 1 to 4 showed that particularly organic sulphonic acids, and also sulphuric acid and the hydrogen salts thereof, are suitable catalysts for the process according to the invention. The conversions of the aldehyde were more than 90% in all examples. In example 4, the conversion was in the same order of magnitude as for a conventional catalyst (CE1); in example 3, the conversion was even higher.

Examples 3-6

The experimental procedure was the same described in examples 1-4, except that the catalyst and also the amount of the catalyst were varied according to Table 2.

TABLE 2

| Example | Catalyst | Amount of catalyst (in mmol) | Molar ratio of aldehyde to catalyst | Conversion of the aldehyde (in GC %) |
|---|---|---|---|---|
| CE 1 | NH$_4$Cl | 5 mmol | 1:0.17 | 98.6 |
| CE 2 | NH$_4$Cl | 2.5 mmol | 1:0.08 | 97.4 |
| 3 | KHSO$_4$ | 5 mmol | 1:0.17 | 99.4 |
| 5 | KHSO$_4$ | 1.1 mmol | 1:0.04 | 99.6 |
| 6 | KHSO$_4$ | 0.4 mmol | 1:0.01 | 99.9 |

CE: Comparative example

Examples 3, 5 and 6 showed clearly that a reduction in the molar amount of catalyst in the process according to the invention allowed the conversions to be enhanced further. In contrast, comparative examples 1 and 2 show that, in the case of use of ammonium chloride—a conventional catalyst—a reduction in the molar amount of catalyst resulted in lower conversions.

Examples 7-11

The experimental procedure was the same as in example 5, except that the amount of methanol and trimethyl orthoformate was varied according to Table 3.

TABLE 3

| | Methanol | | Trimethyl orthoformate | | |
|---|---|---|---|---|---|
| Example | (in ml) | Molar ratio to the aldehyde | (in g) | Molar ratio to the aldehyde | Conversion of the aldehyde (in GC %) |
| 7 | 13.3 | 10.96 | 14.1 | 4.42 | 99.6% |
| 8 | 17.8 | 14.62 | 10.5 | 3.31 | 99.6% |
| 9 | 22.2 | 18.27 | 7.0 | 2.21 | 99.6% |
| 10 | 26.7 | 21.93 | 3.5 | 1.10 | 99.5% |
| 11 | 28.9 | 23.75 | 1.8 | 0.55 | Incomplete conversion Aldehyde dissolves incompletely |

CE: Comparative example

Examples 7 to 11 showed that the orthoformate content may be lowered to a molar ratio of aldehyde to orthoformate of 1:1.1 without the conversion of the aldehyde being impaired.

Example 12

Preparation of the Methoxy-Substituted Quinone Methide

A 35 l glass vessel with stirrer and condenser was charged with 4.0 kg of 3,5-di-tert-butyl-4-hydroxy-benzaldehyde, 2 g of trimethyl orthoformate and 6 kg of methanol were added and the contents mixed. Subsequently, 45 g of sodium hydrogensulphate were added. Then the reaction mixture was heated under reflux for approx. 1 to 2 hours. After one hour, the conversion of the aldehyde was checked by gas chromatography. The aldehyde was converted completely after one hour. The reaction mixture was cooled and filtered through a Schenk filter. The filter residue was washed with 8 kg of ethylbenzene. The filtrate was returned back to the glass stirred tank, and the mixture of methanol, trimethyl orthoformate and ethylbenzene distilled off as rapidly as possible. Subsequently, the azeotropic distillation was commenced, in the course of which 300 to 500 ml of ethylbenzene were added continuously per hour and just as much distillate was removed. After 5 hours, a conversion of 70% was attained; after 9 hours, the conversion to the desired quinone methide increased to more than 90%.

The reaction mixture was cooled. The desired quinone methide precipitated out in the course of cooling and was isolated with a purity of >98%.

Example 13

Preparation of the Butoxy-Substituted Quinone Methide from 3,5-Di-Tert-Butyl-4-Hydroxy-Benzaldehyde 7 g of the 3,5-di-tert-butyl-4-hydroxybenzaldehyde were admixed with 3.5 g of trimethyl orthoformate and 21 g of n-butanol. Subsequently, 0.1 g of potassium hydrogensulphate was added and the reaction mixture heated under reflux for 2 hours. The aldehyde used was converted quantitatively.

Then the potassium hydrogensulphate was filtered off and the filter residue washed with 50 g of ethylbenzene. Subsequently, the mixture of methanol, trimethyl orthoformate and ethylbenzene was distilled off until a boiling temperature of 130° C. was attained. Then 100 ml of ethylbenzene per hour were added constantly, and the same amount of distillate removed simultaneously.

After 6 hours, 82% of the butoxy-substituted quinone methide formed. As a by-product, 7% of the 3,5-di-tert-butyl-4-hydroxybenzaldehyde had formed.

Example 14

Preparation of the Butoxy-Substituted Quinone Methide from the Methoxy-Substituted Quinone Methide 1 g of the methoxy-substituted quinone methide (from example 12) was dissolved in 20 g of ethylbenzene. Then 1 g of n-butanol was added. The reaction mixture was heated under reflux for two hours. According to analysis by gas chromatography, 73% of the methoxy-substituted quinone methide was converted to the butoxy-substituted quinone methide.

Example 15

Preparation of an Aroxy-Substituted Quinone Methide from the Methoxy-Substituted Quinone Methide 1 g of the methoxy-substituted quinone methide was dissolved in 35 g of ethylbenzene. Subsequently, 0.65 g of 4-tert-butylcatechol was added. The reaction mixture was heated under reflux for two hours. According to analysis by gas chromatography, 77% of the methoxy-substituted quinone methide converted to the 4-tert-butylcatechol-substituted quinone methide (aryloxy-substituted).

Examples 16-20

Preparation of 3,5-Di-Tert-Butyl-4-Hydroxybenzaldehyde 2,6-di-tert-butylphenol was dissolved in glacial acetic acid. Subsequently, urotropin and water were added, and the reaction mixture heated at not more than 2° C. below the reflux temperature for 4 to 5 hours. The precipitated product was filtered off and washed with water and methanol, and dried on a rotary evaporator. The molar ratios of the reactants used and also the determined yields of 3,5-di-tert-butyl-4-hydroxybenzaldehyde, based on 2,6-di-tert-butylphenol, are shown in Table 4.

TABLE 4

| | Molar ratio of . . . to 2,6-di-tert-butylphenol | | Molar ratio of acetic acid | Yield (in % based on 2,6-di-tert- |
|---|---|---|---|---|
| Example | Urotropin | Acetic acid | to water | butylphenol) |
| 16 | 0.50 | 14.52 | 1.54 | 60.50 |
| 17 | 0.67 | 14.52 | 1.54 | 82.57 |
| 18 | 0.80 | 14.52 | 1.54 | 89.22 |
| 19 | 0.80 | 12.66 | 1.34 | 89.47 |
| 20 | 1 | 14.52 | 1.54 | 87.46 |

Examples 16 to 19 showed unexpectedly high yields which were not to be expected on the basis of the small amounts of urotropin. These examples showed that a process with a molar ratio of urotropin to the phenol of less than 1 also leads to astonishingly high yields and conversions.

Examples 21-25

Preparation of 3,5-Di-Tert-Butyl-4-Hydroxybenzaldehyde (Variation of the Reaction Temperature)

2,6-di-tert-butylphenol was dissolved in glacial acetic acid. Subsequently, urotropin and water were added, and the reaction mixture heated at different temperatures for 5.5 hours. The precipitated product was filtered off and washed with water and methanol, and dried on a rotary evaporator. The particular reaction temperatures, yields and purities are shown in Table 5.

TABLE 5

| Example | Molar ratio of . . . to 2,6-di-tert-butylphenol Urotropin | Acetic acid | Molar ratio of acetic acid to water | Reaction temperature (in ° C.) | Yield (in % based on 2,6-di-tert-butylphenol) | Purity (in %) |
|---|---|---|---|---|---|---|
| 21 | 1.00 | 7.26 | 1.54 | 118-140 | 91.4 | 72.0 |
| 22 | 1.00 | 7.26 | 1.54 | 118-126 | 92.6 | 96.5 |
| 23 | 1.00 | 7.26 | 1.54 | 117-120 | 90.1 | 99.9 |
| 24 | 1.00 | 14.52 | 1.54 | 118-124 | 88.7 | 98.6 |
| 25 | 1.00 | 14.52 | 1.54 | 109-118 | 83.1 | 45.1 |

Examples 21-25 showed that excessively low reaction temperatures lead to conversion losses, and excessively high reaction temperatures lead to purity problems. In addition, at excessively high reaction temperatures from the reflux temperature, there is the risk that solids will block the column.

German patent application 102009002514.6, filed Apr. 21, 2009, is incorporated herein by reference.

Numerous modifications and variations and variations of the present invention are possible in light of the above description. It is therefore to be understood that within the scope of the appended claims, the invention may be practiced otherwise than as specifically described herein.

The invention claimed is:

1. A process for preparing a substituted 1,4-quinone methide of formula (I)

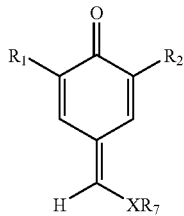

formula (I)

wherein
$R_1$ and $R_2$ are each independently hydrogen, optionally substituted $(C_1-C_{15})$-alkyl, $(C_3-C_{15})$-cycloalkyl or $(C_6-C_{14})$-aryl,
$R_7$ is optionally substituted $(C_1-C_{15})$-alkyl, $(C_3-C_{15})$-cycloalkyl or $(C_6-C_{14})$-aryl, and
X is O or S,
comprising:
reacting a 3,5-disubstituted 4-hydroxybenzaldehyde of formula (II)

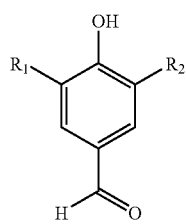

formula (II)

wherein $R_1$ and $R_2$ are each as defined above, with an orthoformate of formula (III)

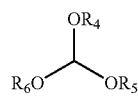

formula (III)

wherein $R_4$, $R_5$ and $R_6$ are each independently optionally substituted $(C_1-C_{15})$-alkyl, $(C_3-C_{15})$-cycloalkyl or $(C_6-C_{14})$-aryl,
and an alcohol and/or thioalcohol ((thio)alcohol) of formula (IV)

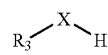

formula (IV)

wherein
$R_3$ is an optionally substituted $(C_1-C_{15})$-alkyl, $(C_3-C_{15})$-cycloalkyl or $(C_6-C_{14})$-aryl, and
X is O or S,
in the presence of a at least one catalyst selected from the group consisting of a free or solid-phase-bound organic sul- phonic acid, sulphuric acid, a hydrogensulphate, an organic or inorganic phosphorus acid, a dihydrogen or hydrogen salt of an organic or inorganic phosphorous acid, fuming nitric acid and boric acid, to obtain a (thio)acetal; and eliminating the alcohol or thiol from the obtained (thio)acetal to yield the substituted 1,4-quinone methide of formula (I).

2. The process according to claim 1,
wherein the at least one catalyst is at least one of a free or solid-phase-bound organic sulphonic acid, sulphuric acid, or a hydrogensulphate.

3. The process according to claim 1, wherein
a molar ratio of the 3,5-disubstituted 4-hydroxybenzalde- hyde to the at least one catalyst is from 1:0.001 to 1:0.1.

4. The process according to claim 1, wherein
a molar ratio of the 3,5-disubstituted 4-hydroxybenzalde- hyde of formula (II) to the orthoformate of formula (III) is from 1:1 to 1:2.

5. The process according to claim 1, wherein
eliminating the (thio)alcohol from the obtained acetal com- prises:
heating the acetal-containing reaction mixture to at least 100° C. to release the (thio)alcohol; and
immediately removing the released (thio)alcohol from the reaction mixture by chemical and/or physical methods.

6. The process according to claim 5, wherein
eliminating the (thio)alcohol from the obtained acetal fur- ther comprises:
after the acetal-containing reaction mixture is heated to at least 100° C., continuously metering into the acetal- containing reaction mixture an additional solvent (C); and
simultaneously removing the (thio)acetal and the solvent (C).

7. A process for preparing a substituted 1,4-quinone methide of formula (V)

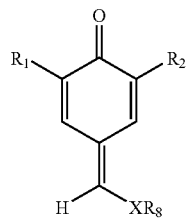

formula (V)

wherein $R_1$ and $R_2$ are each independently hydrogen, optionally substituted $(C_1-C_{15})$-alkyl, $(C_3-C_{15})$-cycloalkyl or $(C_6-C_{14})$-aryl, $R_8$ is an optionally substituted $(C_3\text{-}C_{15})$-alkyl, $(C_3\text{-}C_{15})$-cycloalkyl or $(C_6\text{-}C_{14})$-aryl, and X is O or S, comprising:

reacting a substituted 1,4-quinone methide of formula (I)

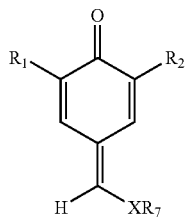

formula (I)

wherein $R_7$ is an unsubstituted $(C_1\text{-}C_2)$-alkyl group,

X is O, and $R_1$ and $R_2$ are each as defined above, with an alcohol or thioalcohol of formula (VI)

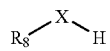

formula (VI)

wherein X is O or S, and $R_8$ is as defined above.

8. The process according to claim 7,
wherein the substituted 1,4-quinone methide of formula (I) is prepared by the process according to claim 1.

9. A process for preparing a 3,5-disubstituted 4-hydroxybenzaldehyde of formula (II)

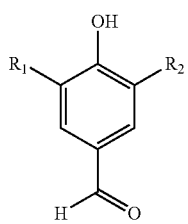

formula (II)

wherein $R_1$, $R_2$ are each independently, hydrogen, optionally substituted $(C_1\text{-}C_{15})$-alkyl, $(C_3\text{-}C_{15})$-cycloalkyl or $(C_6\text{-}C_{14})$-aryl, comprising:

reacting a 2,6-disubstituted phenol of formula (VII)

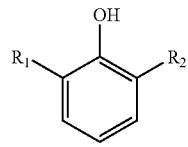

formula (VII)

wherein $R_1$ and $R_2$ are each as defined above,
with urotropin in a solvent mixture consisting of glacial acetic acid and water;

wherein a reaction temperature is maintained at least 2° C. below a reflux temperature of the reaction mixture over the entire reaction time; and wherein a ratio of glacial acetic acid to water is selected such that a reaction temperature of 115° C.±10° C. is obtained without distillation of water.

10. The process according to claim 9,
wherein a molar ratio of the 2,6-disubstituted phenol of formula (VII) to the urotropin is from 1:1 to 1:0.8.

11. The process according to claim 1, wherein $R_1$ and $R_2$ are independently a tert-butyl or isopropyl group.

12. The process according to claim 1, wherein the orthoformate of formula (III) is trimethyl orthoformate.

13. The process according to claim 1, wherein $R_3$, $R_4$, $R_5$ and $R_6$ are identical groups.

14. The process according to claim 1, wherein $R_3$, $R_4$, $R_5$ and are methyl groups.

15. The process according to claim 1, wherein the 4-hydroxybenzaldehyde of formula (II) is converted to the (thio)acetal in the absence of an additional solvent (A).

16. The process according to claim 1, wherein no halogenated compounds are employed as a reactant, solvent or catalyst.

17. The process according to claim 9, wherein $R_1$ and $R_2$ are independently a tert-butyl or isopropyl group.

18. The process according to claim 9, wherein no halogenated compounds are employed as a reactant, solvent or catalyst.

19. The process according to claim 9, wherein a temperature for reacting the 2,6-disubstituted phenol of formula (VII) and urotropin is 115° C.±10° C. over the entire reaction time.

* * * * *